United States Patent [19]
Beaver et al.

[11] 4,151,941
[45] May 1, 1979

[54] MACHINE FOR DETACHING A SURGICAL BLADE FROM A CONTINUOUS STRIP IN WHICH IT IS FORMED AND PRESENTING IT TO A POSITION FOR A SUBSEQUENT OPERATION

[75] Inventors: John R. Beaver, Lexington; George J. Kozlowski, Bedford, both of Mass.

[73] Assignee: Rudolph Beaver, Inc., Belmont, Mass.

[21] Appl. No.: 717,757

[22] Filed: Aug. 25, 1976

[51] Int. Cl.² ............................................. B26F 3/00
[52] U.S. Cl. .................................. 225/97; 225/96.5; 225/103
[58] Field of Search .............. 225/97, 96.5, 103, 105; 29/413

[56] References Cited

U.S. PATENT DOCUMENTS

| | | | |
|---|---|---|---|
| 3,465,935 | 9/1969 | Martin | 225/103 |
| 3,730,412 | 5/1973 | Guell | 225/103 |
| 3,907,185 | 9/1975 | Suzuki | 225/103 X |
| 3,952,931 | 4/1976 | Weber | 225/103 |

Primary Examiner—Frank T. Yost
Attorney, Agent, or Firm—Robert E. Ross

[57] ABSTRACT

A machine for detaching a surgical blade from a continuous strip in which it is manufactured and presenting the blade to a position for assembly into a blade holder. The disclosed embodiment of the invention is designed for use with a continuous strip of material which has blades formed integrally along an edge thereof, and joined thereto by pre-scored lines. The machine breaks the connection between an individual blade and the strip along the pre-scored lines while grasping the blade, and then moves the separated blade to a predetermined position for assembly with a blade holder.

7 Claims, 8 Drawing Figures

MACHINE FOR DETACHING A SURGICAL BLADE FROM A CONTINUOUS STRIP IN WHICH IT IS FORMED AND PRESENTING IT TO A POSITION FOR A SUBSEQUENT OPERATION

BACKGROUND OF THE INVENTION

In certain types of delicate surgical operations, it has been customary to use as a surgical blade a piece of an ordinary carbon steel razor blade of the so-called "safety razor" type. Suitable tools are provided to break off from the blade a shard of desired size, which is then placed into a blade holder. Surgical blades thus made have provided acceptable results in operations such as eye surgery because of the sharpness of the blade and the thinness of the stock from which the blade is formed. The blade is, of course, discarded after a single use.

However, the forming of a blade in this manner and the use thereof has a number of disadvantages. Not every portion of a razor blade edge is suitable for this purpose and the portion to be used must be selected very carefully. The blade shard must be sterilized prior to use, and handled to assemble into the holder, which can cause damage to the cutting edge. Further, the surgeon's glove can be accidentally cut and pinched during these manipulations.

Also, the cutting edge on such a shard is not perfectly straight but has a slight curvature resulting from the bending to cause fracture.

In recent years it has become difficult for surgeons to obtain razor blades suitable for this use because of the shift from carbon steel blades to stainless steel blades. Although a piece of a carbon steel blade of proper size can be readily broken off by a suitable tool with a simple bending motion because of the brittleness of the blade, the material of which the stainless steel blades is formed is not as brittle, and hence such blades do not break cleanly, but break with a severe curve imparted to the broken edge. Hence the separation of a piece of desired size from such a blade is sufficiently difficult to be an impractical method of forming a surgical blade with an uncurved cutting tip.

In a co-pending application of the present joint inventors, Ser. No. 678,866 filed Apr. 21, 1976, there is disclosed a surgical blade and method of manufacture thereof, in which the blade is made in continuous strip form with the blade being so attached to the strip at scored portions so that it is easily separated therefrom at a predetermined position, providing a blade portion sharpened along one side edge and a tang extending laterally therefrom for use in positioning the blade in a holder. After separation from the strip the blade is assembled into a slot in the end of a suitable holder, and secured therein by heat deformation of the plastic or by an adhesive, or in any other convenient manner.

SUMMARY OF THE INVENTION

The object of this invention is to provide a machine for receiving a continuous strip carrying pre-formed blades as described in the above-identified application and hereafter, indexing the strip so that individual blades are positioned sequentially at work stations where a first score line is broken to partially separate the blade from the strip, the blade is grasped by a suitable mechanism, the blade is then separated completely from the strip by breaking along another connecting score line and the mechanism then moves the blade away from the strip into position for assembly with a suitable holder.

DESCRIPTION OF THE ILLUSTRATED EMBODIMENT

Figure 1:
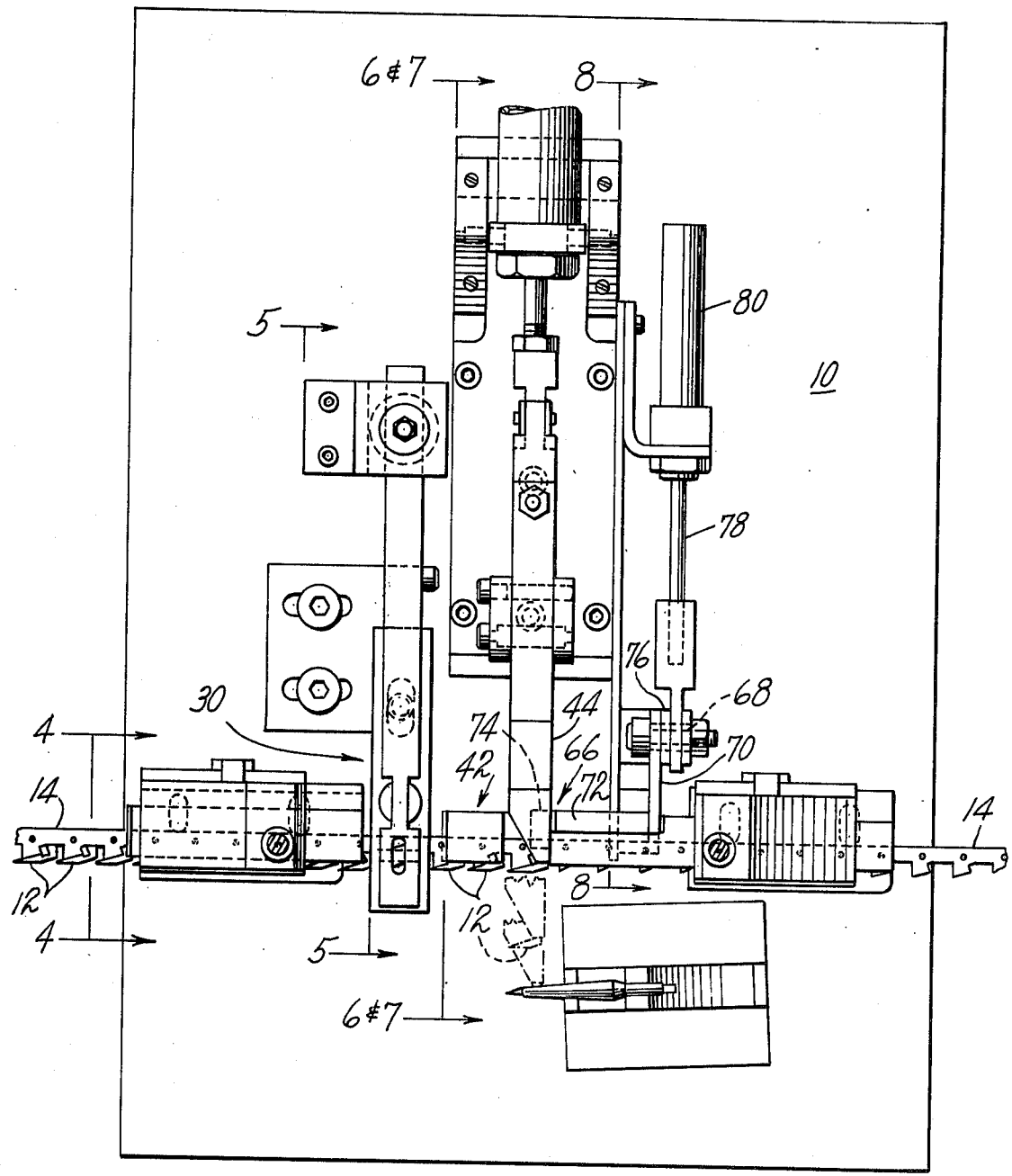
FIG. 1 is a top plan view of a machine embodying the features of the invention.
Figure 2:
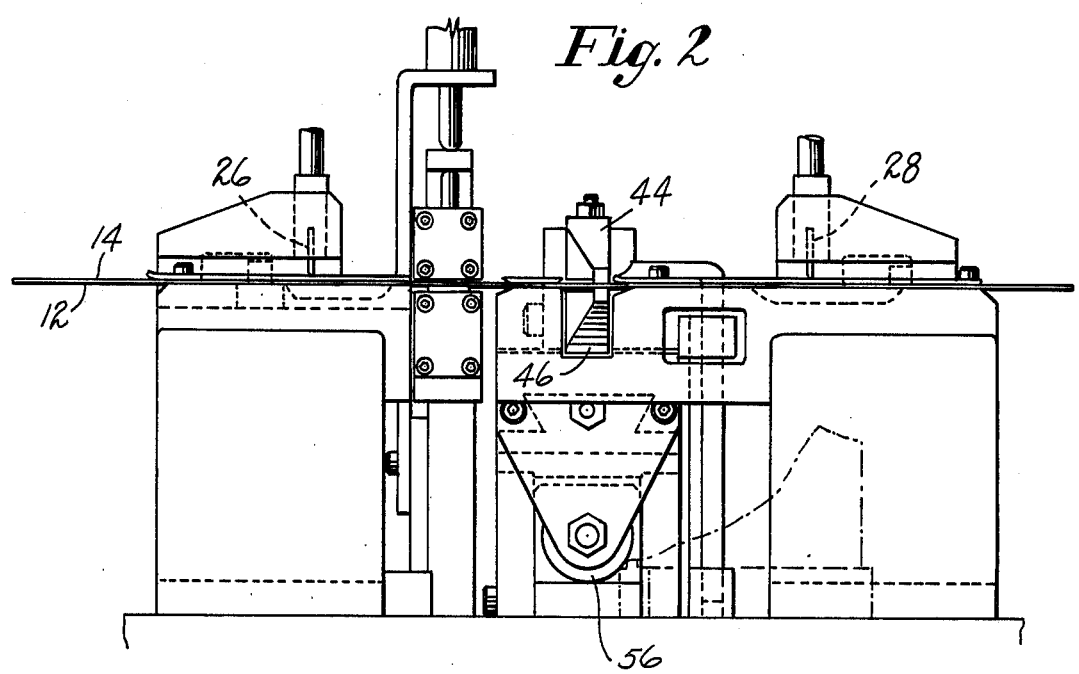
FIG. 2 is a view in front elevation of the machine of FIG. 1.

Referring to the drawings, there is illustrated a machine 10 which is particularly adapted for separating individual blades 12 from a continuous strip 14.

Figure 3:
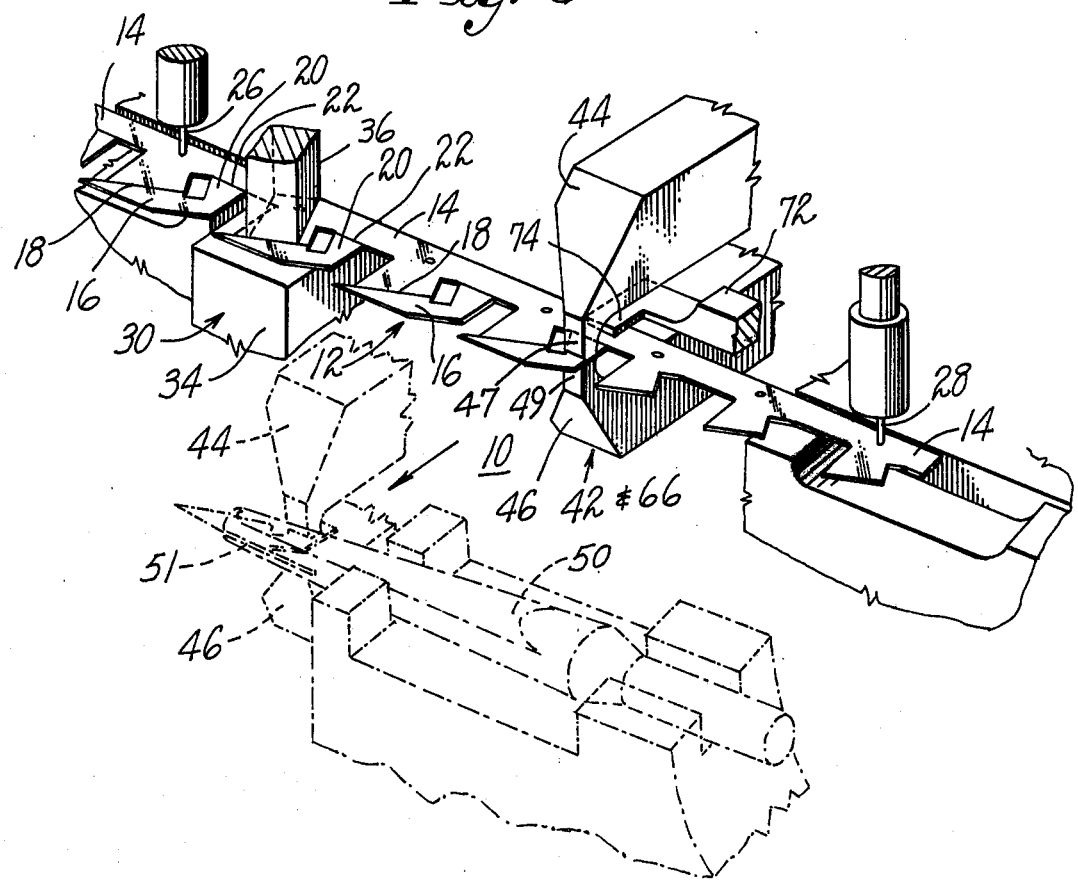
FIG. 3 is a perspective view of the work stations of the machine of FIGS. 1 and 2, with the forward position of the blade grasping mechanism being shown in phantom line.
Figure 4:
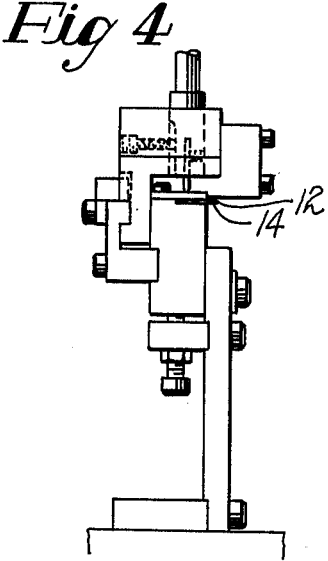
FIG. 4 is a view taken on line 4—4 of FIG. 1.

In the illustrated embodiment the blades are formed from the strip by punching out strip portions, forming a blade portion 16 joined to the strip by a scored line 18, and a tang 20 joined to the strip (see FIG. 3) by a scored line 22. The outer edge 24 of the blade portion is parallel to the axis of the strip and is sharpened to provide the cutting edge of the blade.

The machine 10 is provided with strip pilot pins 26 and 28 at the entrance and exit respectively of the machine, which are operated by suitable mechanism (not shown) in timed relation to other machine mechanisms in the usual manner to position the strip in proper relation to said other machine mechanisms during the operating cycle thereof.

The strip 14 may be moved longitudinally by any suitable feed and indexing mechanism known in the art (not shown) which also operates in timed relation to the other machine mechanisms so that on each cycle of the machine the strip moves forwardly a distance equal to the blade spacing on the strip.

Figure 5:
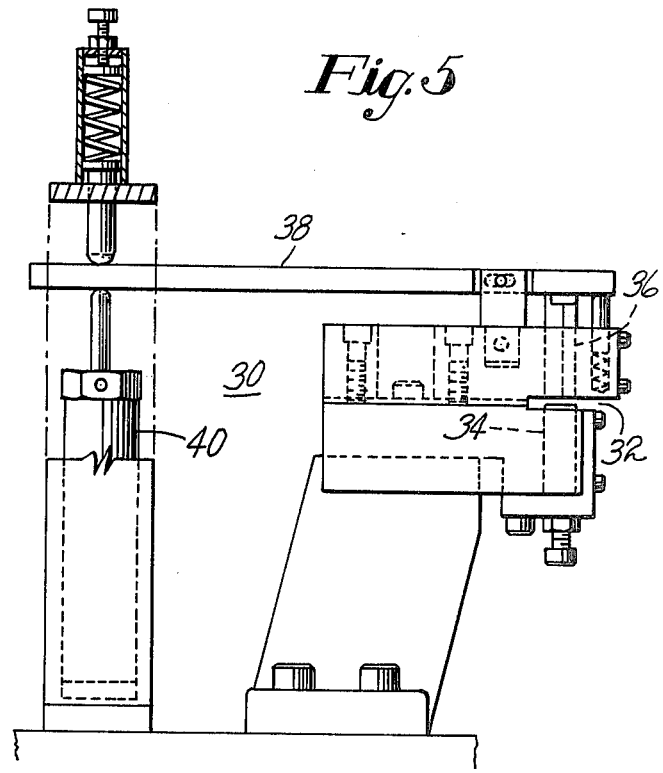
FIG. 5 is a view taken on line 5—5 of FIG. 1, illustrating a work station at which a first score line connecting the blade to the strip is broken.

The machine 10 comprises a first work station 30 (see FIGS. 3 and 5) which comprises a slot 32 through which the strip 14 passes, a lower stationary die 34, and an upper die 36 which is movable downwardly against the strip by any suitable mechanism such as by a pivoted arm 38 actuated by an air cylinder 40.

The upper and lower dies 34 and 36 are shaped and positioned in relation to the strip 14 in the slot 32 so that actuation of the air cylinder 40 to move the upper die 36 downwardly breaks the score line 18 so that the blade portion 16 of the blade 12 is separated from the strip.

A second work station 42 is provided with a pair of jaws 44 and 46 having opposed blade grasping projections 48 at the outer ends thereof.

The jaws 44 and 46 are movable from a retracted and open position, (see FIG. 6) in which the projections 47 and 49 are positioned on opposite sides of the tang portion 20 of a blade, and a forward and closed position in which a blade retained between the projections is positioned for assembly with a blade holder 50.

The jaws 44 and 46 are mounted on a carrier 52 which is slidable forwardly and rearwardly on a support 54 by an air cylinder 56.

Figure 6:
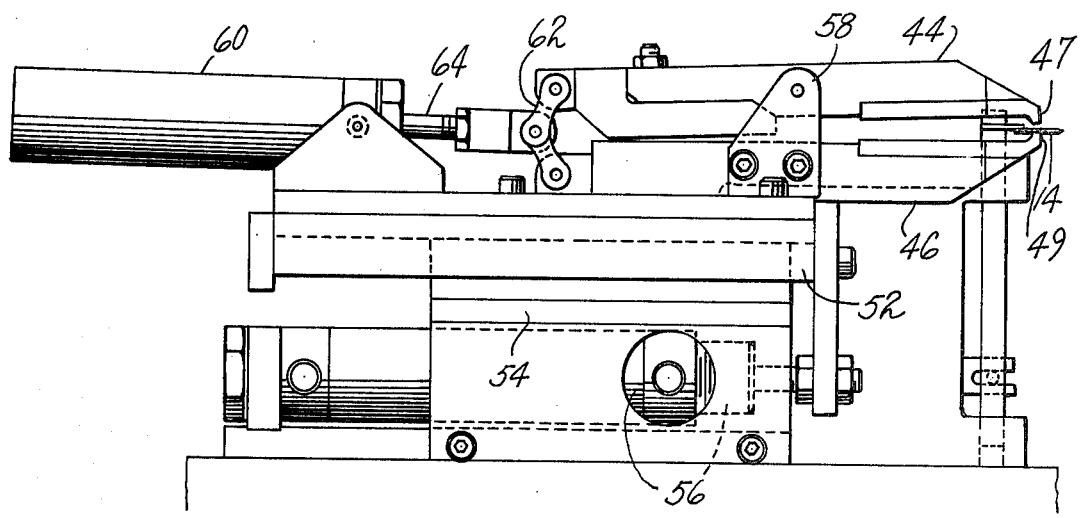
FIG. 6 is a view taken on line 6—6 of FIG. 1, illustrating the blade grasping mechanism in the retracted and open position.
Figure 7:
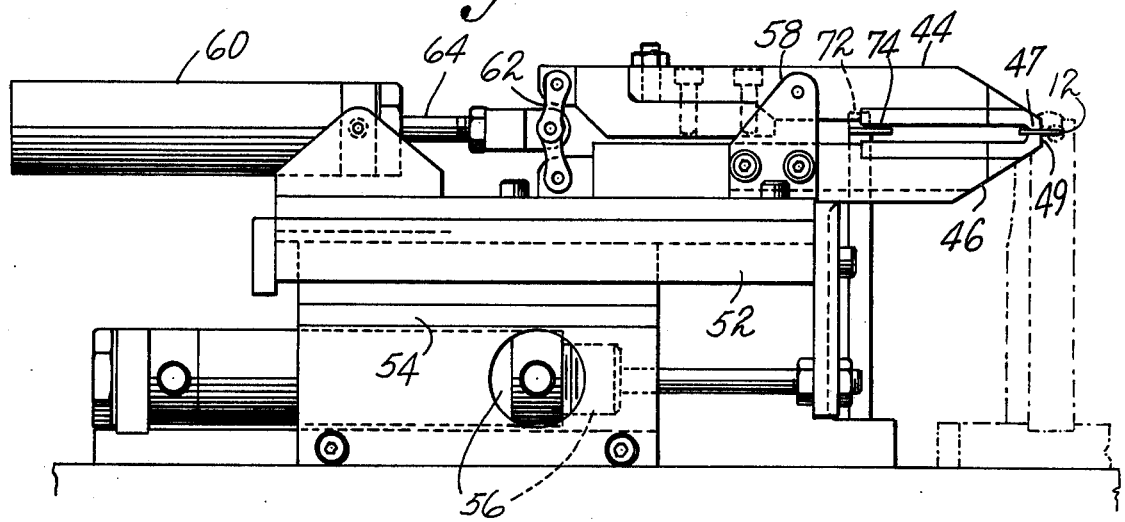
FIG. 7 is a view taken on line 7—7 of FIG. 1 showing the blade grasping mechanism in the forward position, after having grasped a blade prior to separation from the strip and moved it forwardly into position for assembly with a blade holder.
Figure 8:
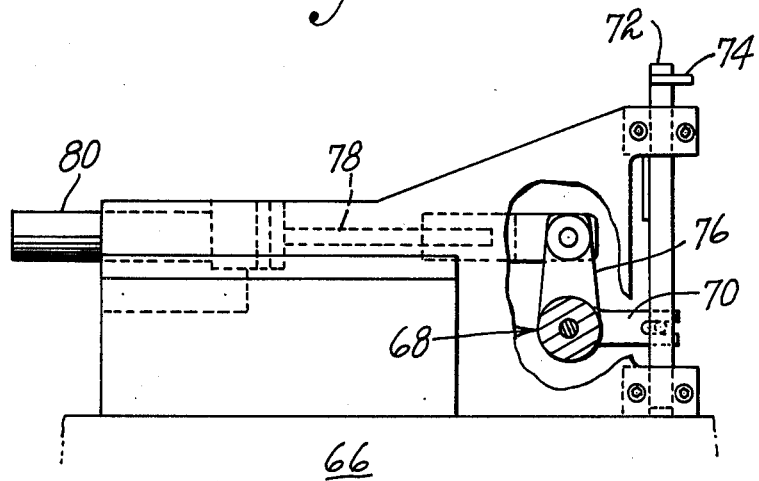
FIG. 8 is a view taken on line 8—8 of FIG. 1, illustrating a work station at which a second and final score line connecting the blade to the strip is broken, while the blade is grasped by the mechanism of FIG. 7.

The lower jaw 46 is fixed to the carrier 52, and the upper jaw 44 is medially pivoted to a bracket 58. The jaws are opened and closed by means of an air cylinder 60 operating a linkage 62, so that forward motion (to the right, as seen in FIGS. 6 and 7) of the air cylinder rod 64 closes the jaws to the position of FIG. 7.

The actuating means (not shown) for the air cylinders 56 and 60 is so timed that the cylinder 60 is actuated to close the jaws 44 and 46 to grasp the blade tang 20, and subsequently the cylinder 56 is actuated to move the jaw mechanism forwardly to position the blade in relation to the blade holder.

However, between the time of actuation of the cylinder 60 and the cylinder 56, the mechanism of a third work station 66 is actuated to break the remaining connection between the blade and the strip at score line 22.

The work station 66 comprises a crank pivoted at 68, said arm having a forwardly extending portion 70 carrying a laterally extending member 72 with a presser foot 74 which is positioned between the jaws 46 and 48 and over the strip 14. The crank has an operating lever 76 which is connected to the piston rod 78 of an air cylinder 80.

The actuating means of the air cylinder 80 is timed to extend the piston rod to rotate the crank so that the presser foot moves down against the strip adjacent to the score line 22 just after the projections 47 and 49 have grasped the tang 20. This motion of the presser foot 74 breaks the material along the score line 22 thereby completely separating the blade from the strip.

The jaws thereafter move forwardly, carrying the separated blade in the manner previously described.

The specific form of the blade holder 50 and the manner of retaining the blade in the holder does not form part of the present invention. In the illustrated embodiment the holder 50 is formed of plastic and has a slot 51 in the forward end to receive the blade. The blade may be retained thereafter in the holder in any suitable manner, such as by heat deformation of the plastic or by adhesives. The tang 20, used to position the blade in the holder, may be removed in a secondary operation.

Since certain changes apparent to one skilled in the art may be made in the specific embodiment of the invention illustrated and described herein, it is intended that all matter contained herein be interpreted in an illustrative and not a limiting sense.

I claim:

1. A machine for separating at a predetermined weakened portion a sharpened knife blade from a continuous strip in which the blade is formed and presenting it to a position for a subsequent operation, comprising means for positioning the strip, other means for grasping the blade, means for separating the blade from the strip at the weakened portion, and means for thereafter moving said other means in a direction to carry the blade away from the strip.

2. A machine as set out in claim 1 in which the means for grasping the blade comprises a pair of jaws straddling the strip, said jaws being pivoted on one side of the strip and having opposing means on the ends thereof for clamping the blade therebetween, said jaws being shaped and dimensioned to provide an aperture therebetween such that the jaws, while straddling the strip can move the clamped blade away from the strip.

3. A machine as set out in claim 1 which includes means actuated while the blade is being grasped to move the strip relative to the blade, said means being positioned in relation to the strip so that such movement causes the blade to break away from the strip along the weakened portion.

4. A machine for detaching pre-formed blades from a continuous strip on which said blades comprise a blade portion and a tang portion each attached to the strip at scored portions, said machine comprising a predetermined path along which the strip may be indexed, means at a first work station at a first position along the predetermined path for separating the blade portion from the strip at a first connecting scored portion, clamp means at a second work station at a subsequent position along the predetermined path for grasping the tang and means at said second work station for detaching the tang from the strip at a second connecting scored portion while it is grasped by the clamp means, and means for thereafter moving the clamp means in a direction to move the detached blade away from the strip.

5. A machine as set out in claim 4 in which said clamp means, when grasping the tang, forms an aperture through which the strip passes, said aperture being dimensioned to allow movement of the clamp means to carry the detached blade away from the strip in a direction generally perpendicular to the axis thereof.

6. A machine as set out in claim 4 in which the means at the work stations for separating the blade portion and the tang from the strip comprise cooperating members positioned and operable to apply a breaking force to occur along the score lines.

7. A machine for detaching from a continuous strip a pre-formed and sharpened surgical blade having a blade portion spaced from the main body of the strip and connected to a lateral extension of the strip by a portion having a weakened portion, and a tang portion extending laterally from the blade portion and connected to the strip at a weakened portion, said machine comprising a first work station having means operable to apply a breaking force to the weakened portion connecting the blade portion to the lateral extension of the strip, a second work station having means to grasp the tang, means to thereafter apply a breaking force to the weakened portion connecting the tang to the strip while the tang is being grasped, and means for thereafter moving the grasping means in a direction to move the blade laterally away from the strip.

* * * * *